(12) United States Patent
MacDonald

(10) Patent No.: US 10,287,514 B2
(45) Date of Patent: May 14, 2019

(54) METHOD AND APPARATUS FOR RECOVERING SYNTHETIC OILS FROM COMPOSITE OIL STREAMS

(71) Applicant: PNG Gold Corporation, Vancouver (CA)

(72) Inventor: Martin R. MacDonald, Plano, TX (US)

(73) Assignee: Gen III Oil Corporation, Vancouver (CA)

( * ) Notice: Subject to any disclaimer, the term of this patent is extended or adjusted under 35 U.S.C. 154(b) by 0 days.

(21) Appl. No.: 15/428,195

(22) Filed: Feb. 9, 2017

(65) Prior Publication Data

US 2017/0152449 A1    Jun. 1, 2017

Related U.S. Application Data

(63) Continuation of application No. 14/169,113, filed on Jan. 30, 2014.

(Continued)

(51) Int. Cl.
*C10G 53/04* (2006.01)
*C07C 5/02* (2006.01)
(Continued)

(52) U.S. Cl.
CPC ............... *C10G 53/04* (2013.01); *C07C 5/02* (2013.01); *C07C 7/005* (2013.01); *C10G 7/00* (2013.01); *C10G 7/003* (2013.01); *C10G 7/006* (2013.01); *C10G 21/006* (2013.01); *C10G 21/02* (2013.01); *C10G 21/16* (2013.01); *C10G 21/18* (2013.01); *C10G 21/20* (2013.01); *C10G 21/24* (2013.01); *C10G 45/04* (2013.01); *C10G 53/06* (2013.01);

(Continued)

(58) Field of Classification Search
None
See application file for complete search history.

(56) References Cited

U.S. PATENT DOCUMENTS

| 3,173,859 A | 3/1965 | Chambers |
|---|---|---|
| 3,625,881 A | 12/1971 | Chambers |

(Continued)

FOREIGN PATENT DOCUMENTS

| RU | 2330873 C2 | 8/2008 |
|---|---|---|
| RU | 2008142984 A | 5/2010 |

(Continued)

OTHER PUBLICATIONS

The Office Action dated Sep. 15, 2014 by Canadian Intellectual Property Office for the corresponding Canadian patent application No. 2,845,176.

(Continued)

*Primary Examiner* — Tam M Nguyen
(74) *Attorney, Agent, or Firm* — MBM Intellectual Property Law LLP

(57) ABSTRACT

A method for recovering synthetic oils from a feed stream, the method comprising separating at least a portion of the non-synthetic oil constituents from a commingled stream to produce a partially purified synthetic oil stream and one or more contaminant streams. Extracting at least a portion of the synthetic oil from the partially purified synthetic oil stream to produce a synthetic oil stream and a second contaminant stream.

5 Claims, 3 Drawing Sheets

Related U.S. Application Data

(60) Provisional application No. 61/774,027, filed on Mar. 7, 2013, provisional application No. 61/774,037, filed on Mar. 7, 2013.

(51) Int. Cl.

| | |
|---|---|
| *C07C 7/00* | (2006.01) |
| *C10G 21/16* | (2006.01) |
| *C10G 21/18* | (2006.01) |
| *C10G 21/20* | (2006.01) |
| *C10G 21/24* | (2006.01) |
| *C10G 45/04* | (2006.01) |
| *C10G 67/04* | (2006.01) |
| *C10G 67/14* | (2006.01) |
| *C10G 21/02* | (2006.01) |
| *C10G 7/00* | (2006.01) |
| *C10G 21/00* | (2006.01) |
| *C10G 53/06* | (2006.01) |
| *C10G 53/08* | (2006.01) |
| *C11B 3/00* | (2006.01) |

(52) U.S. Cl.
CPC ............. *C10G 53/08* (2013.01); *C10G 67/04* (2013.01); *C10G 67/14* (2013.01); *C11B 3/006* (2013.01); *C10G 2300/1007* (2013.01); *C10G 2300/44* (2013.01); *C10G 2400/22* (2013.01); *C10G 2400/30* (2013.01)

(56) References Cited

U.S. PATENT DOCUMENTS

| | | |
|---|---|---|
| 3,923,644 A | 12/1975 | Hindman |
| 4,001,807 A | 1/1977 | Dallimonti |
| 4,021,333 A | 5/1977 | Habiby et al. |
| 4,033,859 A | 7/1977 | Davidson et al. |
| 4,071,438 A | 1/1978 | O'Blassny |
| 4,101,414 A | 7/1978 | Kim et al. |
| 4,151,072 A | 4/1979 | Nowack et al. |
| 4,169,044 A | 9/1979 | Crowley |
| 4,233,140 A | 11/1980 | Antonelli et al. |
| 4,302,325 A | 11/1981 | Fletcher et al. |
| 4,342,645 A | 8/1982 | Fletcher et al. |
| 4,360,420 A | 11/1982 | Fletcher et al. |
| 4,399,025 A | 8/1983 | Fletcher et al. |
| 4,431,524 A | 2/1984 | Norman |
| 4,432,856 A | 2/1984 | Norman |
| 4,512,878 A | 4/1985 | Reid et al. |
| 4,894,140 A | 1/1990 | Schon |
| 4,941,967 A | 7/1990 | Mannetje et al. |
| 5,028,313 A | 7/1991 | Kalnes et al. |
| 5,045,179 A | 9/1991 | Langhoff et al. |
| 5,049,258 A | 9/1991 | Kelm et al. |
| 5,102,531 A | 4/1992 | Kalnes et al. |
| 5,143,597 A | 9/1992 | Sparks et al. |
| 5,242,579 A | 9/1993 | Mead et al. |
| 5,244,565 A | 9/1993 | Lankton et al. |
| 5,302,282 A | 4/1994 | Kalnes et al. |
| 5,306,419 A | 4/1994 | Harrison et al. |
| 5,362,381 A | 11/1994 | Brown et al. |
| 5,382,328 A | 1/1995 | Drespa et al. |
| 5,384,037 A | 1/1995 | Kalnes |
| 5,447,625 A | 9/1995 | Harrison et al. |
| 5,632,867 A | 5/1997 | Davis et al. |
| 5,707,510 A | 1/1998 | Berry |
| 5,759,385 A | 6/1998 | Aussillous et al. |
| 5,795,462 A | 8/1998 | Shurtleff |
| 5,814,207 A | 9/1998 | Kenton |
| 5,871,618 A | 2/1999 | Lee et al. |
| 5,885,444 A | 3/1999 | Wansborough et al. |
| 5,904,838 A | 5/1999 | Kalnes et al. |
| 5,980,698 A | 11/1999 | Abrosimov et al. |
| 6,007,701 A | 12/1999 | Sherman et al. |
| 6,106,699 A | 8/2000 | MacDonald et al. |
| 6,117,309 A | 9/2000 | Daspit et al. |
| RE36,922 E | 10/2000 | Sparks et al. |
| 6,132,596 A | 10/2000 | Yu |
| 6,174,431 B1 | 1/2001 | Williams et al. |
| 6,179,999 B1 | 1/2001 | Sherman et al. |
| 6,238,551 B1 | 5/2001 | Sherman et al. |
| 6,292,737 B1 | 9/2001 | Higashimata et al. |
| 6,319,394 B2 | 11/2001 | Sherman et al. |
| 6,320,090 B1 | 11/2001 | Sherman et al. |
| 6,372,122 B1 | 4/2002 | Gorman |
| 6,398,948 B1 | 6/2002 | Sherman et al. |
| 6,402,937 B1 | 6/2002 | Shaffer, Jr. et al. |
| 6,440,298 B1 | 8/2002 | Shurtleff |
| 6,512,147 B2 | 1/2003 | Inaba et al. |
| 6,592,748 B2 | 7/2003 | Cody et al. |
| RE38,366 E | 12/2003 | Kenton |
| 6,712,954 B1 | 3/2004 | Pohler et al. |
| 6,713,438 B1 | 3/2004 | Baillargeon et al. |
| 6,805,062 B2 | 10/2004 | Shurtleff |
| 6,929,737 B2 | 8/2005 | Sherman et al. |
| 7,226,533 B2 | 6/2007 | Aramburu |
| 7,261,808 B2 | 8/2007 | Grandvallet et al. |
| 7,267,760 B2 | 9/2007 | Sherman et al. |
| 8,366,912 B1 | 2/2013 | MacDonald |
| 2001/0001198 A1 | 5/2001 | Sherman et al. |
| 2001/0022281 A1 | 9/2001 | Sherman et al. |
| 2001/0025807 A1 | 10/2001 | Sherman et al. |
| 2002/0036158 A1 | 3/2002 | Austin |
| 2004/0011704 A1 | 1/2004 | Shurtleff |
| 2005/0004239 A1 | 1/2005 | Bull et al. |
| 2005/0006282 A1 | 1/2005 | Grandvallet et al. |
| 2006/0211907 A1 | 9/2006 | Pieter De Wet et al. |
| 2008/0000808 A1 | 1/2008 | Sherman et al. |
| 2011/0278151 A1 | 11/2011 | MacDonald |
| 2014/0257008 A1* | 9/2014 | MacDonald ............. C07C 5/02 585/802 |
| 2017/0130143 A1* | 5/2017 | MacDonald ............. C07C 5/02 |

FOREIGN PATENT DOCUMENTS

| | | |
|---|---|---|
| SU | 969169 A | 10/1982 |
| WO | 03060040 A2 | 7/2003 |
| WO | 2004080929 A2 | 9/2004 |
| WO | 2006/096396 | 9/2006 |

OTHER PUBLICATIONS

The Supplementary International Search Report or Declaration dated Mar. 27, 2015 by Russian Patent Office for corresponding PCT application PCT/IB2014/000462.
The Supplementary International Search Report or Declaration dated May 28, 2015 by European Patent Office for corresponding PCT application PCT/IB2014/000462.
The Notice of Allowance dated Apr. 8, 2016 by Canadian Intellectual Property Office for the corresponding Canadian patent application No. 2,845,176.
Canadian Patent Office; Office Action; Canadian Application No. 2,845,176; dated May 14, 2014, 2 pages.
Canadian Patent Office; International Search Report and Written Opinion; PCT Application No. PCT/IB2014/000462, dated Jul. 16, 2014, 13 pages.
"Standard Guide for Characterizing Hydrocarbon Lubricant Base Oils", The American Society for Testing Materials, ASTM D6074-08, Nov. 2008.
"Engine Oil Licensing and Certification Systems Specification", American Petroleum Institute, API 1509, 14th Edition, Dec. 1996.
U.S. Appl. No. 15/416,069 Office Action dated Mar. 22, 2018.

* cited by examiner

METHOD AND APPARATUS FOR RECOVERING SYNTHETIC OILS FROM COMPOSITE OIL STREAMS

RELATED APPLICATIONS

The present application claims priority to U.S. Provisional Patent Application No. 61/774,027, filed Mar. 7, 2013 and U.S. Provisional Patent Application No. 61/774,037, filed Mar. 7, 2013, and is related to U.S. Pat. No. 8,366,912, issued Feb. 5, 2013, which are hereby incorporated by reference for all purposes as if set forth herein in their entirety.

TECHNICAL FIELD

The present disclosure relates to the recovery of synthetic oils, and more specifically to the recovery of synthetic oils from blended, composite or contaminated streams.

BACKGROUND OF THE INVENTION

Large volumes of synthetic oils are produced world-wide, but are typically discarded after use.

SUMMARY OF THE INVENTION

A method for recovering synthetic oils from a feed stream is provided. The method includes separating at least a portion of the non-synthetic oil constituents from a commingled stream to produce a partially purified synthetic oil stream and one or more contaminant streams. At least a portion of the synthetic oil is separated from the partially purified synthetic oil stream to produce a synthetic oil stream and a second contaminant stream.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE SEVERAL VIEWS OF THE DRAWINGS

Aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views, and in which.

DETAILED DESCRIPTION OF THE INVENTION

Figure 1:
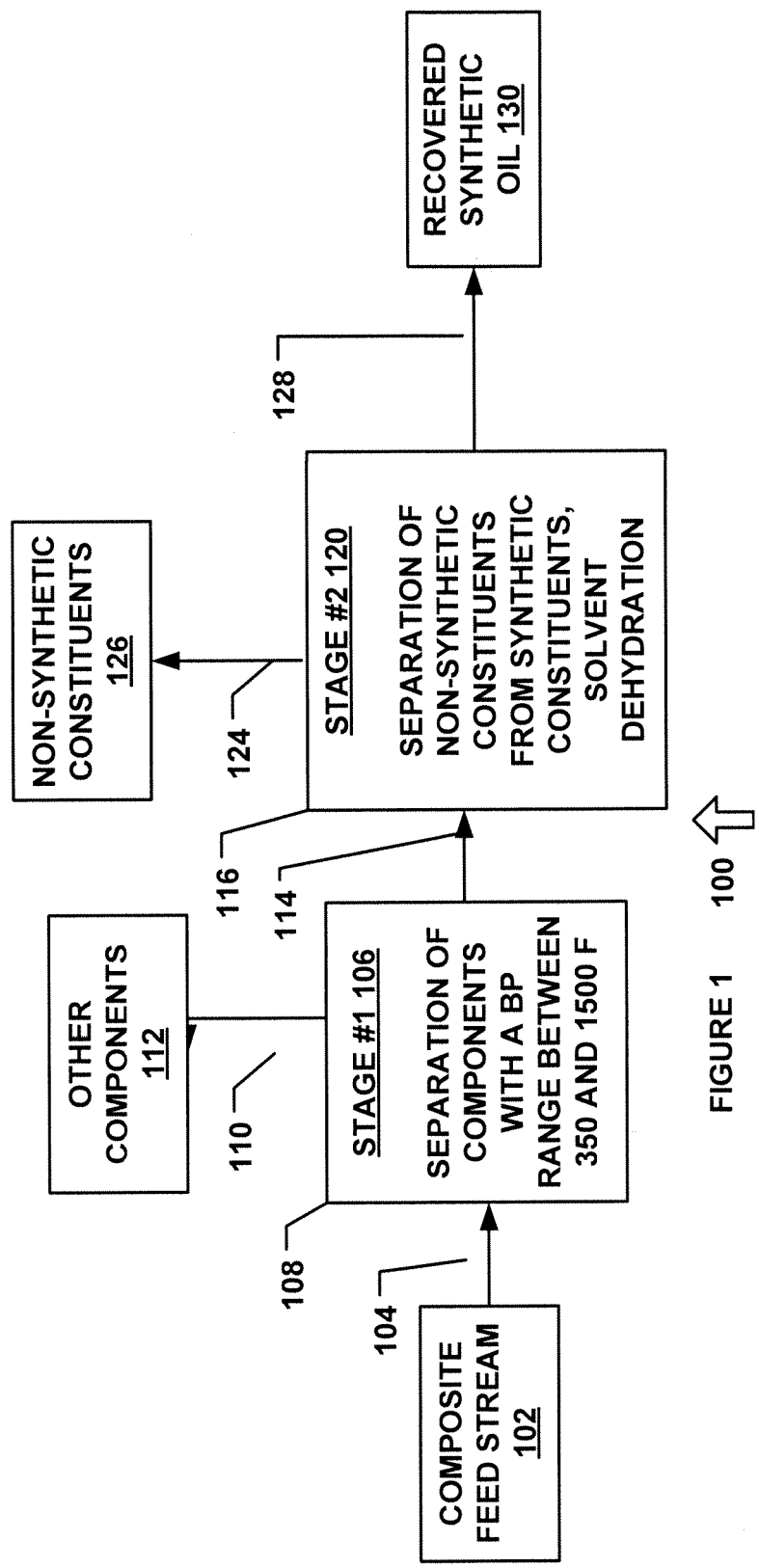
FIG. 1 is a diagram of a system for recovering synthetic oil from a waste oil stream, in accordance with an exemplary embodiment of the present disclosure.

In the description that follows, like parts are marked throughout the specification and drawings with the same reference numerals. The drawing figures might not be to scale and certain components can be shown in generalized or schematic form and identified by commercial designations in the interest of clarity and conciseness.

Synthetic oils such as polyalphaolefins have unique thermal, electrical, lubricating, and chemical stability properties that make them suitable for a number of diverse uses, such as: a heat transfer medium in chillers, heaters, transformers, and engines; a seal material in vacuum equipment and pumps; a lubricant in turbines, combustion engines, chains, and mechanical equipment; a constituent in greases and metalworking fluids; and a component of cosmetics, food stuffs and medical supplies. There are several different means of producing such synthetic oils. The type of synthetic oil is generally defined by the process or the chemical precursors used to manufacture the synthetic oil. For example, polyalphaolefins can be synthesized by the oligomerization of 1-decene or other alphaolefin monomers, which are combined to form longer chain molecules. Ester-based synthetic oils can be made from ester precursors. Other synthetic oils can be manufactured using gas to liquid technologies whereby methane molecules are combined to form longer chain molecules. Additionally, some synthetic oil molecules can be manufactured by chemical reformation of petroleum streams, such as isomerization processes. The synthetic oil produced by each of these processes is consistent in chemical structure and physical properties.

Synthetic oils, through blending, usage and/or handling, can become contaminated with oxidation and degradation products, water, fuels, solvents, chemicals, petroleum products, fine particulates and the like. Service can also result in changes in the molecular structure of some of the synthetic oil molecules, thereby changing the original nature and performance of these molecules. These contaminants or changed molecules may reduce the desired performance of the synthetic stream as a whole, potentially rendering the composite stream unsuitable for its intended use. Contaminated synthetic oil is typically removed from pipelines, equipment or storage and considered waste.

The present disclosure concerns the recovery of composite oil streams, contaminated oil streams, blended oil streams, waste industrial fluid streams or other oil sources that contain synthetic oil. With advancements in technology, the amount of synthetic oils produced and used in the United States and around the world has increased to the point where such use has become significant. Currently, the vast majority of the composite, contaminated, blended or waste synthetic oil is combined with industrial fuels and burned as a combustion fuel. This practice not only contributes significant pollutants to the environment, but also wastes the energy and resources that were used to generate these valuable synthetic streams from their precursors. Accordingly, the present disclosure recognizes the need to recover and reuse these synthetic streams. The disclosed synthetic oil recovery process recovers a high percentage of the available synthetic molecules in the contaminated, composite, blended or waste oil stream in an environmentally friendly, economically viable and commercially sound manner.

FIG. 1 is a diagram of a system 100 for recovering synthetic oil from a waste oil stream, in accordance with an exemplary embodiment of the present disclosure. A composite stream 102 consisting of at least a portion of synthetic oil line in addition to non-synthetic oil is charged to a contaminant separation zone 108, where contaminants with a molecular weight of less than 200 or greater than 15,000 or a boiling point less than around 500° F. and greater than around 1200° F., line 110, is separated from the components that have a molecular weight between around 200 to around 15,000 or a boiling point between around 500° F. and 1200° F., line 114. The materials recovered through line 110 can be low molecular weight materials such as light hydrocarbons, water, glycols, and the like, typically having a boiling range generally below about 500° F. and high molecular weight materials and non-volatiles including particulates, polymers, heavy petroleum product, salts, and the like, typically having a boiling point greater than about 1200° F. A portion of the synthetic oil constituents are recovered through a line 114. This stream typically consists of molecules with a molecular weight of around 200 to around 15,000 typically having a boiling point between about 500 to about 1200° F. In a further separation zone 116, a portion of the synthetic oil is separated and recovered through a line 128. Line 128 is primarily synthetic oil typically consisting of one or more of polyalphaolefins, esters and other types of synthetic oil molecules. A second stream line 124, which is oil that is low in synthetic oil molecules, is also produced. This is a relatively generalized showing of the process of the present disclosure.

In the first stage, zone 106, some of the physical contaminants are separated from the synthetic oil. Typically, such contaminants include water, light hydrocarbons, solvents, solids, polymers, high molecular weight hydrocarbons, chemicals, salts, non-volatiles, and the like. Several processes or combination of processes can be used to effect this separation including various forms of extraction, distillation, filtration, centrifugation, absorption and adsorption, and the like, as known to those skilled in the art. Typically, the separation will take place based upon differences in the physical or chemical properties of the synthetic oil fraction and the various contaminating materials. In the second stage, the partially purified synthetic oil stream, line 114, is then fed to zone 116 of the process where the remaining contaminants are removed from the synthetic oil. One or more of the following processes can be used to effect separation of the synthetic oil stream 128 from the non-synthetic oil components. These processes include one or more of various forms of solvent extraction, supercritical extraction, ultra-filtration, absorption, adsorption, molecular sieves, and the like, as known to those skilled in the art. Dehydration of the solvent used in solvent extraction is performed to reduce absorbed water to a much smaller percentage of solvent than would normally be used, such as to less than 0.1 percent as compared to 1 to 2 percent. This increased dehydration improves the quality of the synthetic oil stream 128, even though the overall process efficiency may be lower than processes that utilize solvent with more dissolved water. The synthetic oil stream can be sold as a product to be used wherever synthetic oils are typically used or may be further treated to separate the synthetic oil into two or more synthetic oil fractions differing in one or more of molecular weight, morphology, chemical composition or physical properties.

Figure 2:
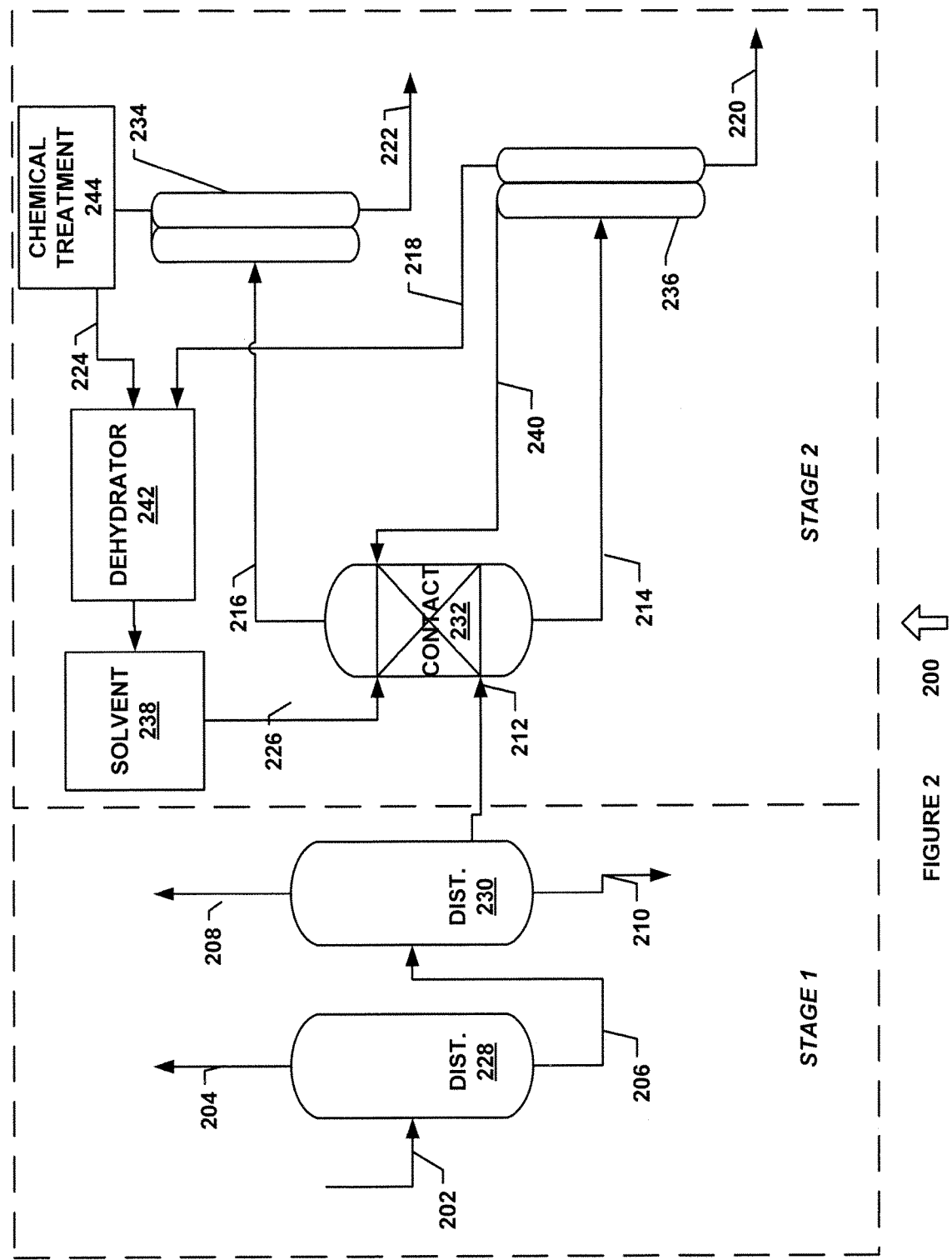
FIG. 2 is a diagram of system for separating synthetic oil from a waste oil stream in accordance with an exemplary embodiment of the present disclosure.

FIG. 2 is a diagram of system 200 for separating synthetic oil from a waste oil stream in accordance with an exemplary embodiment of the present disclosure. In Stage 1, a distillation system 228 is shown for separating materials that have a boiling point less than 500° F., line 204, from the composite stream, line 202, thereby producing a partially purified synthetic and non-synthetic oil stream. The distillation system 228 consists of one or more vessels which may be operated under vacuum or at pressure and can be single or multiple staged as known to those skilled in the art. Stream 204 generally consists of one or more contaminants that have alow boiling point, such as water, light hydrocarbons, glycols, solvents, and other volatile materials such as might be found to have been combined with the synthetic molecules. The low boiling point contaminants can also contain breakdown products from the synthetic oil. In certain rigorous applications, it is possible for the synthetic molecules to split into two or more smaller molecules. One or more of these may be volatile below 50° F. and would end up in stream 204. In the instances where the synthetic oil has not split or contaminated with volatile materials, the flow of stream 204 can be minimal or zero.

The composite stream line 206 consists of the material that generally has a boiling point greater than 500° F. This stream discharges from the bottom of distillation system 228 and is optionally heated and charged into a second distillation system 230. The second distillation system 230 consists of one or more distillation devices such as columns, evaporators, or the like, known to those skilled in the art for fractionating streams based on boil point. The distillation devices can be operated under vacuum and/or at pressure and can be single or multiple staged as known to those skilled in the art. In distillation system 230, at least a portion of the molecules having a boiling point between 500° F. and 1,200° F. are separated from the balance of the composite stream. The compounds having a boiling point less than 500° F. pass from the distillation devices whereon they are condensed and collected. The compounds with a boiling point generally greater than 1200° F. are separated from the compounds with a boiling point between 500° F. and 1200° F. by distillation or in other suitable manners and exit the second distillation system through line 210. The compounds that have a boiling point generally between 500° F. and 1200° F., or partially purified synthetic oil, exit the second distillation system through line 212 and are passed to the second stage of the process.

The second stage of the process consists of solvent extraction and recovery. The stream in line 212 is generally passed through a cooler to a solvent treating vessel 232. This solvent treating vessel is shown with a top and a bottom. A contact section is shown schematically in the center portion of the vessel. A solvent storage vessel is shown at 238 and supplies solvent to an upper portion of vessel 232 near its top via a line 226. The solvent moves downwardly, countercurrent to the partially purified synthetic oil stream via a line 212, which is introduced near the bottom of contact section. Upon contact, the solvent does not react with the synthetic molecules, however, it does react with the non-synthetic molecules cleaving to them and causing them to be extracted from the synthetic molecules.

The synthetic oil molecules are recovered with a portion of the solvent from the top of vessel 232 and passed via a line 216 to first solvent separation vessels 234, which each have a top and a bottom, where the solvent is separated from the synthetic oil molecules and the synthetic oil is passed via a line 222 to product storage. The use of multiple vessels increases the efficiency of the synthetic oil separation process. Contact vessel 232 can have multiple injection points in the vessel or associated columns, to control the solvent concentration in the vessel or associated columns. Line 222 thus contains purified synthetic oil stream which can be used in a number of applications wherein synthetic oils are used. Contact vessel 232 can be operated at a temperature range that is close to the stability limit at which the solvent and oil become completely miscible. In one exemplary embodiment, the temperature range can be controlled to that there are points within contact vessel 232 where the temperature stability limit is exceeded, and the solvent and oil become completely miscible, but where the temperature at other points is below the stability limit.

The solvent is recovered through a line 224, and is typically treated to remove water, low boiling point contaminants, and the like through dehydrator 242 and returned to solvent storage 238. The amount of water removed from the solvent is not limited, as is common in known processes, where the water content is used to improve the quality of non-synthetic oil. However, with the increasing use of synthetic oil, waste oil typically contains a greater amount of synthetic oil that is of greater value than the non-synthetic oil. As such, even though removal of as much water from the solvent as possible results in a decrease in the efficiency of the process (due to increasing energy and processing requirements for the dehydration process), and also results in less efficient processing of non-synthetic oil, the use of solvent with small amounts of dissolved water results in an improved quality of synthetic oil extraction.

The solvent recovery process can result in the buildup of organic acids as the solvent is reused. These organic acids can corrode the parts of system 200, and can be removed with chemical treatment system 244, which can process the solvent with caustic materials to neutralize the organic acids.

A bottom stream 214 is recovered from vessel 232 and passed to a second solvent separation vessels 236, each of which have a top and a bottom. In vessels 236, the solvent is stripped from the extracted primarily non-synthetic contaminant and passed via a line 218 back to solvent storage 238. The non-synthetic contaminants recovered from the bottom of vessel 236 are passed via a line 220 to storage. In addition, a line 240 from one or more of the first of the second solvent separation vessels 236 is provided back to vessel 232. This line is relatively rich in solvent, even though it contains some extracted non-synthetic oil compounds and other compounds, and can be provided to vessel 232 to improve the overall process efficiency by reducing the amount of solvent that is processed through dehydrator 242.

In the embodiment described in Stage 1 above, two distillation systems are used to separate a portion of the contaminants from the synthetic oil fraction. In accordance with the present disclosure, it may be desirable to use as few as one or as many as five distillation systems, each consisting of one or more vessels to effect this separation.

In the embodiment described above, prior to the first vessel of Stage 1, an optional treatment vessel can be used to chemically treat the composite stream prior to entry into distillation system 224 to facilitate treatment. This chemical treatment can be an alkali or base material such as sodium carbonate, sodium bicarbonate, sodium hydroxide, potassium hydroxide, or an acid such as sulfuric acid, or other chemicals known to reduce the amount of the composite stream components that cause fouling, to enhance separation and processing, to increase equipment availability and to enhance the quality of the synthetic oil or other products.

In Stage 1 of the embodiment described above, vessels are used to separate various constituents from the synthetic oil fraction. These vessels can include simple evaporators, thin or wiped film evaporators, columns, packed columns, vessels, tanks, pipes or any suitable vessel or system that effects single or multiple stages of separation. These vessels may be operated under vacuum or pressure.

In the practice of the present invention, it may be desirable in some instances for the boiling point of stream 212 to be between about 650 and 1200° F. The boiling point range of the material recovered through line 212 can be modified if desired to produce a synthetic oil product having a slightly higher initial boiling point or the like. Additionally, if desired, a distillation column can be used to fractionate the synthetic oil stream 222 into different fractions.

In some instances, it may be preferable to create more than one partially purified synthetic oil stream from distillation column 230, differing in terms of distillation profile. In this instance, one or more storage vessels can be used between Stage 1 and Stage 2 and the material passed to Stage 2 on a blocked out basis. Thus Stage 2 would be used to purify each of the streams individually. While one first partially purified synthetic oil stream is being processed through Stage 2, the other stream(s) are accumulated in intermediate storage tanks. When the first stream tank is close to being emptied, Stage 2 can then be used to process the content of a second intermediate storage tank containing a second partially purified synthetic oil stream.

In the embodiment described above, Stage 2 is used to separate the similar molecular weight contaminants from the synthetic oil molecules. In certain instances, it may also be possible to further upgrade the contaminant stream through further processing such as filtration, chemical treatment, or extraction using a different solvent, hydrogenation or other suitable processes.

In the embodiment shown above, the solvent recovered from the synthetic oil stream 216 and the contaminant stream 214 are consolidated in a solvent storage vessel 238. Either prior to vessel 234 or post vessel 238, the solvent can be treated to remove any contaminants such as water or similar boiling point materials that may have contaminated the solvent. Such treatments include distillation, extraction, absorption, adsorption, osmosis, chemical treatment or other suitable treatments.

In Stage 1 of the embodiment shown above, distillation system 228 typically consists of one or more distillation vessels, which are operated under vacuum ranging from full vacuum to 500 mmHg and preferably between 2 and 30 mmHg and at a temperature generally between about 500 and about 750° F.

In the second stage of the embodiment shown above, the extraction process used in vessel 232 can include solvent extraction, with materials such as ethanol, diacetone-alcohol, ethylene-glycol-mono(low alkyl) ether, di-ethylene-glycol, diethylene-glycolmono(low alkyl) ether, o-chlorophenol furfural, acetone, formic acid, 4-butyrolacetone, low-alkyl-ester of low mono- and dicarbonic acids, dimethylformamide, 2-pyrrolidone and N-(low alkyl)2-pyrrolidone, N-methyl-2-pyrolodone, epi-chlorohydrin, dioxane, morpholine, low-alkyl and amino(low-alkyl)morpholine, benzonitrile and di-(low-alkyl)sulfoxide and phosphonate, or other suitable separation processes.

N-methyl-2-pyrolodone can also be used as a solvent for the process of the present disclosure. In this embodiment, extraction is undertaken at a temperature between about 100° F. and about 250° F. and preferably between about 130° F. and about 190° F. Typically, both the solvent and partially purified synthetic oil are fed into the extraction column within this temperature range, although not necessarily at the same temperature. The solvent dosage (percent of solvent relative to feed) fed to the extraction column is typically between 50% and 1000% by volume and preferably between 100% and 400%. Typically, extraction is undertaken in a packed or trayed column whereby the solvent is fed into the top of the column and partially purified synthetic oil is fed into the bottom. The packed column can contain structured packing, random packing or other suitable packing. Water may be injected into the solvent or extraction column as desired to control solvent selectivity. Similarly, temperature gradients or regional heating or cooling can be used at various points along or across the extraction column to affect performance and selectivity. Recycles of both raffinate and extract at similar or different temperatures can also be employed. In some instances, it may be beneficial to remove a side stream from the extraction column, raffinate or extract streams cool, and separate a portion of the solvent from the oil and return the oil to the column. The solvent may be recovered from the raffinate stream in line and the extract stream in line using distillation. The distillation can be undertaken atmospherically or by using vacuum. Flash separators or multi-stage columns can be used or combinations thereof can be used in order to separate the solvent from the synthetic oil or the extracted contaminants.

In the exemplary embodiment described above, additional processing may be undertaken on the distillate stream from vessel 228 such as further separating the constituents of this stream (water, glycols, solvents, light hydrocarbons), thereby creating separate products which may be used or further upgraded to higher quality products. In the disclosed embodiment, only one distillate cut is taken from vessel 228.

It may also be suitable in some instances to use a phase transfer catalyst or the like to enhance the operation of the second stage of the process whereby the efficiency, selectivity, and other attributes of the process are enhanced, thereby providing for better separation of the high quality base oil molecules from the lower quality molecules.

By the process of the present disclosure, the synthetic oil stream is separated from a composite stream wherein the synthetic oil is contaminated with other non-synthetic oil materials. The combination of these steps results in a process that is able to recover synthetic oils which heretofore have not been recovered. The recovered synthetic oil is available for reuse in many of its originally intended fields of service. Hence the present disclosure has the benefits of recovering a valuable product stream and reducing demand for the synthesis of virgin streams from their precursors.

Figure 3:
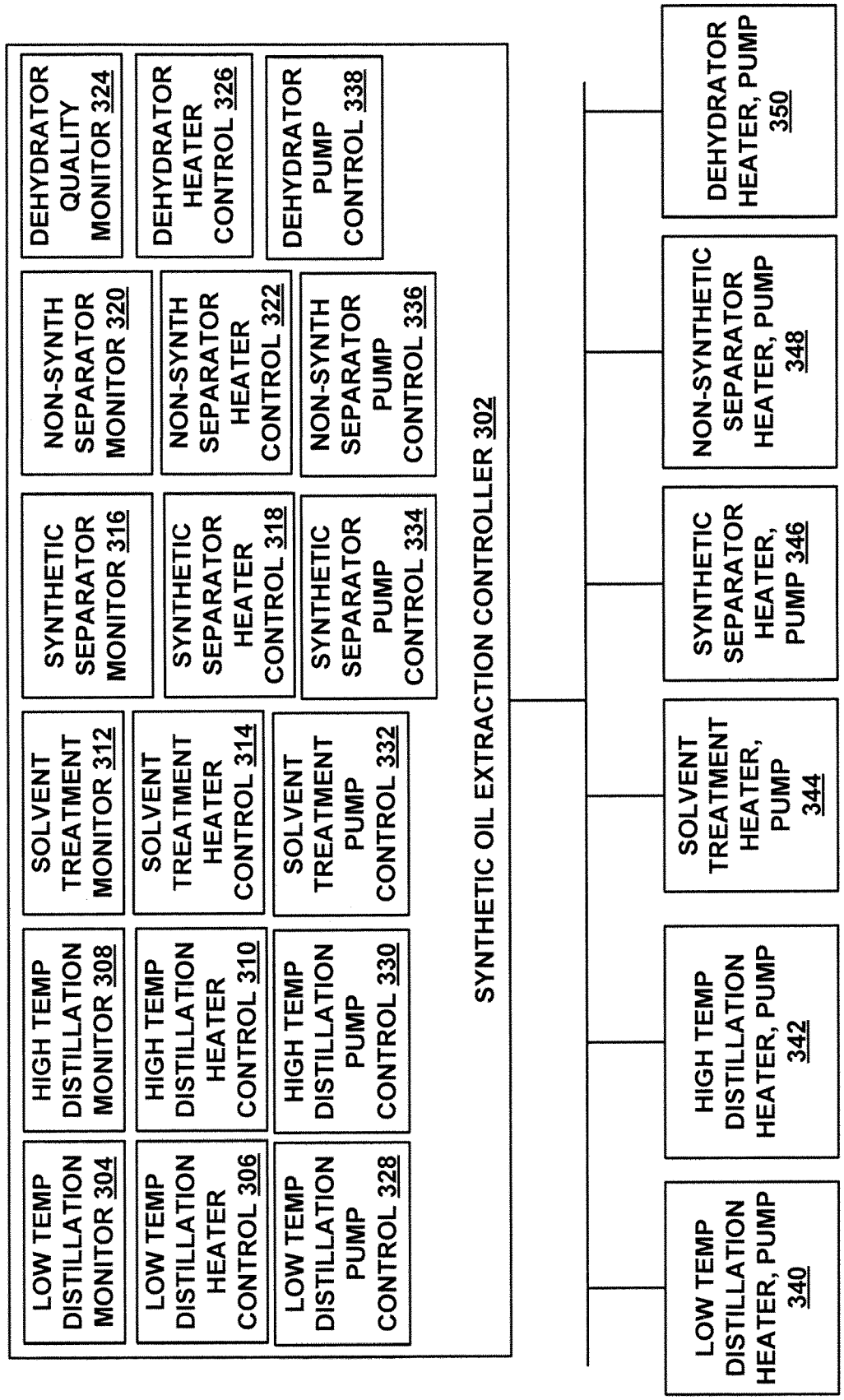
FIG. 3 is a diagram of a controller for controlling a synthetic oil extraction process from waste oil in accordance with an exemplary embodiment of the present disclosure.

FIG. 3 is a diagram of a controller 300 for controlling a synthetic oil extraction process from waste oil in accordance with an exemplary embodiment of the present disclosure. Controller 300 can be implemented in hardware or a suitable combination of hardware and software, and can include one or more software systems operating on a processor.

As used herein, "hardware" can include a combination of discrete components, an integrated circuit, an application-specific integrated circuit, a field programmable gate array, or other suitable hardware. As used herein, "software" can include one or more objects, agents, threads, lines of code, subroutines, separate software applications, two or more lines of code or other suitable software structures operating in two or more software applications, on one or more processors (where a processor includes a microcomputer or other suitable controller, memory devices, input-output devices, displays, data input devices such as keyboards or mice, peripherals such as printers and speakers, associated drivers, control cards, power sources, network devices, docking station devices, or other suitable devices operating under control of software systems in conjunction with the processor or other devices), or other suitable software structures. In one exemplary embodiment, software can include one or more lines of code or other suitable software structures operating in a general purpose software application, such as an operating system, and one or more lines of code or other suitable software structures operating in a specific purpose software application. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections.

System 300 includes synthetic oil extraction controller 302, which includes low temperature distillation monitor 304, high temperature distillation monitor 308, solvent treatment monitor 312, synthetic separator monitor 316, non-synthetic separator monitor 320, dehydrator quality monitor 324, low temperature distillation heater controller 306, high temperature distillation heater controller 310, solvent treatment heater controller 314, synthetic separator heater controller 318, non-synthetic separator heater controller 322, dehydrator heater controller 326, low temperature distillation pump controller 328, high temperature distillation pump controller 330, solvent treatment pump controller 332, synthetic separator pump controller 334, non-synthetic separator pump controller 336 and dehydrator pump controller 338, each of which can be implemented as one or more objects having associated graphical and functional characteristics. Consolidation of these monitors and controls in a single location, display panel or set of display panels allows process variables to be readily monitored and coordinated, unlike separate systems in different locations that have to be monitored and adjusted over time. Such separate systems can have process variations that are not observed by a single operator, which can result in lower quality, lower efficiency or other problems. These problems are more pronounced and significant when processing waste oil with high amounts of synthetic oil compounds, because the quality of the waste oil and the composite compounds of the waste oil can be highly variable, which can make it difficult to adjust process variables over time.

Low temperature distillation monitor 304 generates one or more low temperature distillation metrics, such as temperature, pump speed, pressure, flow rate or other suitable metrics. In one exemplary embodiment, low temperature distillation monitor 304 can include one or more user-selectable controls that allow a user to display or hide a metric, to increase the size of a display for a metric, to add an audible alarm for a metric, or other suitable functions.

High temperature distillation monitor 308 generates one or more high temperature distillation metrics, such as temperature, pump speed, pressure, flow rate or other suitable metrics. In one exemplary embodiment, high temperature distillation monitor 308 can include one or more user-selectable controls that allow a user to display or hide a metric, to increase the size of a display for a metric, to add an audible alarm for a metric, or other suitable functions.

Solvent treatment monitor 312 generates one or more solvent metrics, such as pump speed, pressure, flow rate or other suitable metrics. In one exemplary embodiment, solvent treatment monitor 312 can include one or more user-selectable controls that allow a user to display or hide a metric, to increase the size of a display for a metric, to add an audible alarm for a metric, or other suitable functions.

Synthetic separator monitor 316 generates one or more synthetic separator metrics, such as temperature, pump speed, pressure, flow rate or other suitable metrics. In one exemplary embodiment, synthetic separator monitor 316 can include one or more user-selectable controls that allow a user to display or hide a metric, to increase the size of a display for a metric, to add an audible alarm for a metric, or other suitable functions.

Non-synthetic separator monitor 320 generates one or more non-synthetic separator metrics, such as temperature, pump speed, pressure, flow rate or other suitable metrics. In one exemplary embodiment, non-synthetic separator monitor 320 can include one or more user-selectable controls that allow a user to display or hide a metric, to increase the size of a display for a metric, to add an audible alarm for a metric, or other suitable functions.

Dehydrator quality monitor 324 generates one or more evaporator quality metrics, such as temperature, pump speed, pressure, flow rate or other suitable metrics. In one exemplary embodiment, dehydrator quality monitor 324 can include one or more user-selectable controls that allow a user to display or hide a metric, to increase the size of a display for a metric, to add an audible alarm for a metric, or other suitable functions.

Low temperature distillation heater controller 306 generates one or more user-selectable controls for low temperature distillation heater and pump 340, such as an increase temperature control, a decrease temperature control or other suitable controls. In one exemplary embodiment, low temperature distillation heater controller 306 can interface with low temperature distillation monitor 304 to perform a suitable function in response to an alarm or setting, such as to increase a temperature in response to a low temperature alarm or setting, to decrease a temperature in response to a high temperature alarm or setting, or to perform other suitable functions.

High temperature distillation heater controller 310 generates one or more user-selectable controls for high temperature distillation heater and pump 342, such as an increase temperature control, a decrease temperature control or other suitable controls. In one exemplary embodiment, high temperature distillation heater controller 310 can interface with high temperature distillation monitor 308 to perform a suitable function in response to an alarm or setting, such as to increase a temperature in response to a low temperature alarm or setting, to decrease a temperature in response to a high temperature alarm or setting, or to perform other suitable functions.

Solvent treatment heater controller 314 generates one or more user-selectable controls for solvent treatment valve and pump 344, such as an increase temperature control, a decrease temperature control or other suitable controls. In one exemplary embodiment, solvent treatment heater controller 314 can interface with solvent treatment monitor 312 to perform a suitable function in response to an alarm or setting, such as to increase a temperature in response to a low temperature alarm or setting, to decrease a temperature in response to a high temperature alarm or setting, or to perform other suitable functions.

Synthetic separator heater controller 318 generates one or more user-selectable controls for synthetic separator heater and pump 346, such as an increase temperature control, a decrease temperature control or other suitable controls. In one exemplary embodiment, synthetic separator heater controller 318 can interface with synthetic separator monitor 316 to perform a suitable function in response to an alarm or setting, such as to increase a temperature in response to a low temperature alarm or setting, to decrease a temperature in response to a high temperature alarm or setting, or to perform other suitable functions.

Non-synthetic separator heater controller 322 generates one or more user-selectable controls for non-synthetic separator heater and pump 348, such as an increase temperature control, a decrease temperature control or other suitable controls. In one exemplary embodiment, non-synthetic separator heater controller 322 can interface with non-synthetic separator monitor 320 to perform a suitable function in response to an alarm or setting, such as to increase a temperature in response to a low temperature alarm or setting, to decrease a temperature in response to a high temperature alarm or setting, or to perform other suitable functions.

Dehydrator heater controller 326 generates one or more user-selectable controls for dehydrator heater and pump 350, such as an increase temperature control, a decrease temperature control or other suitable controls. In one exemplary embodiment, dehydrator heater controller 326 can interface with dehydrator quality monitor 324 to perform a suitable function in response to an alarm or setting, such as to increase a temperature in response to a low temperature alarm or setting, to decrease a temperature in response to a high temperature alarm or setting, or to perform other suitable functions.

Low temperature distillation pump controller 328 generates one or more user-selectable controls for low temperature distillation heater and pump 340, such as an increase pump speed control, a decrease pump speed control or other suitable controls. In one exemplary embodiment, low temperature distillation pump controller 328 can interface with low temperature distillation monitor 304 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

High temperature distillation pump controller 330 generates one or more user-selectable controls for high temperature distillation heater and pump 342, such as an increase pump speed control, a decrease pump speed control or other suitable controls. In one exemplary embodiment, high temperature distillation pump controller 330 can interface with high temperature distillation monitor 308 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Solvent treatment pump controller 332 generates one or more user-selectable controls for solvent treatment heater and pump 344, such as an increase pump speed control, a decrease pump speed control or other suitable controls. In one exemplary embodiment, solvent treatment pump controller 332 can interface with solvent treatment monitor 312 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Synthetic separator pump controller 334 generates one or more user-selectable controls for synthetic separator heater and pump 346, such as an increase pump speed control, a decrease pump speed control or other suitable controls. In one exemplary embodiment, synthetic separator pump controller 334 can interface with synthetic separator monitor 316 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Non-synthetic separator pump controller 336 generates one or more user-selectable controls for non-synthetic separator heater and pump 348, such as an increase pump speed control, a decrease pump speed control or other suitable controls. In one exemplary embodiment, non-synthetic separator pump controller 336 can interface with non-synthetic separator monitor 320 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Dehydrator pump controller 338 generates one or more user-selectable controls for dehydrator heater and pump 350, such as an increase pump speed control, a decrease pump speed control or other suitable controls. In one exemplary embodiment, dehydrator pump controller 338 can interface with dehydrator quality monitor 324 to perform a suitable function in response to an alarm or setting, such as to increase a pump speed and change associated valve settings in response to a low pressure alarm or setting, to decrease a pump speed and change associated valve settings in response to a high pressure alarm or setting, or to perform other suitable functions.

Low temperature distillation heater and pump 340 can include one or more heaters, pumps, valves, chillers, compressors and other associated components of a low temperature distillation apparatus such as distillation 228. Although exemplary systems for heater and pump control are described herein, additional systems for individual or group control of valves, chillers, compressors or other components can also or alternatively be provided.

High temperature distillation heater and pump 342 can include one or more heaters, pumps, valves, chillers, compressors and other associated components of a high temperature distillation apparatus such as distillation 230. Although exemplary systems for heater and pump control are described herein, additional systems for individual or group control of valves, chillers, compressors or other components can also or alternatively be provided.

Solvent treatment heater and pump 344 can include one or more heaters, pumps, valves, chillers, compressors and other associated components of a solvent treatment apparatus such as 232. Although exemplary systems for heater and pump control are described herein, additional systems for individual or group control of valves, chillers, compressors or other components can also or alternatively be provided.

Synthetic separator heater and pump 346 can include one or more heaters, pumps, valves, chillers, compressors and other associated components of a synthetic separator apparatus such as separator 234. Although exemplary systems for heater and pump control are described herein, additional systems for individual or group control of valves, chillers, compressors or other components can also or alternatively be provided.

Non-synthetic separator heater and pump 348 can include one or more heaters, pumps, valves, chillers, compressors and other associated components of a non-synthetic separator apparatus such as separator 236. Although exemplary systems for heater and pump control are described herein, additional systems for individual or group control of valves, chillers, compressors or other components can also or alternatively be provided.

Dehydrator heater and pump 350 can include one or more heaters, pumps, valves, chillers, compressors and other associated components of a dehydrator apparatus such as dehydrator 242. Although exemplary systems for heater and pump control are described herein, additional systems for individual or group control of valves, chillers, compressors or other components can also or alternatively be provided.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A system for recovering synthetic oil from a feed stream comprising:
   a first stage comprising a plurality of distillation systems, each distillation system configured to remove compounds having a predetermined boiling point or molecular weight to separate at least a portion of non-synthetic oil constituents from a commingled stream to produce a partially purified synthetic oil stream and one or more contaminant streams;
   a solvent extraction stage comprising a solvent extraction system configured to receive the partially purified synthetic oil stream and to separate at least a portion of the synthetic oil from the partially purified synthetic oil by solvent extraction with solvent having less than 0.1 percent absorbed water to produce a synthetic oil stream and a second contaminant stream; and
   a dehydrator stage coupled to the solvent extraction stage, the dehydrator stage configured to generate solvent having less than 0.1 percent absorbed water for use in the solvent extraction system,
   wherein the dehydrator stage comprises a solvent separator configured to separate a first solvent stream from the synthetic oil stream, and/or a non-synthetic oil separator configured to separate second solvent stream from the second contaminant stream, and
   a dehydrator configured to receive a solvent comprising the first separated solvent stream and/or the second separated solvent and to reduce the amount of absorbed water in the solvent to less than 0.1 percent.

2. The system of claim 1, wherein the non-synthetic oil separator comprises at least one return line coupled to the solvent extraction stage and configured to provide a mix of separated solvent and non-synthetic oil directly to the solvent extraction stage.

3. A controller coupled to the first stage and the solvent extraction stage of claim 1 comprising:
   one or more user selectable controls for modifying a monitor for the first stage;
   one or more user selectable controls for modifying a monitor for the solvent extraction stage;
   one or more user-selectable controls for controlling the first stage;
   one or more user-selectable controls for controlling the solvent extraction stage; and
   wherein each of the user-selectable controls are displayed on a single display board.

4. The controller of claim 3, further comprising:
   one or more user-selectable controls for modifying a monitor for the dehydrator stage; and
   one or more user-selectable controls for controlling the dehydrator stage.

5. The controller of claim 4, wherein the one or more user-selectable controls for controlling the dehydrator stage comprise:
   a pump controller for controlling a speed of a dehydrator stage pump; and a heater controller for controlling a temperature of a dehydrator stage heater.

* * * * *